United States Patent [19]

Nakai et al.

[11] Patent Number: 5,702,698
[45] Date of Patent: Dec. 30, 1997

[54] METHODS OF USE OF IL-1α

[75] Inventors: Satoru Nakai; Mayumi Kaneta; Yoshikazu Kikumoto, all of Tokushima-ken; Yeong-Man Hong, Naruto; Kazuyoshi Kawai, Tokushima-ken; Setsuko Takegata, Tokushima; Kiyoshi Ishii, Tokushima-ken; Yasuo Yanagihara, Tokushima; Yoshikatsu Hirai, Tokushima-ken, all of Japan

[73] Assignee: Otsuka Pharmaceutical Co., Ltd., Tokyo, Japan

[21] Appl. No.: 461,733

[22] Filed: Jun. 5, 1995

Related U.S. Application Data

[62] Division of Ser. No. 252,229, Jun. 1, 1994, Pat. No. 5,543,140, which is a division of Ser. No. 643,292, Jan. 22, 1991, Pat. No. 5,371,204, which is a division of Ser. No. 23,373, Mar. 9, 1987, Pat. No. 5,008,374.

[30] Foreign Application Priority Data

| Mar. 14, 1986 | [JP] | Japan | 61-57885 |
| Jun. 3, 1986 | [JP] | Japan | 61-129759 |
| Jun. 25, 1986 | [JP] | Japan | 61-148393 |
| Jul. 8, 1986 | [JP] | Japan | 61-160250 |
| Aug. 27, 1986 | [JP] | Japan | 61-200323 |

[51] Int. Cl.$^6$ ............................................. A61K 38/20
[52] U.S. Cl. .............................. 424/85.2; 514/2; 514/8; 530/351
[58] Field of Search ...................... 424/85.2; 530/351; 514/2, 8

[56] References Cited

U.S. PATENT DOCUMENTS

| 4,512,974 | 4/1985 | Moldawer et al. | 424/85.2 |
| 4,542,017 | 9/1985 | Moldawer et al. | 424/85.2 |
| 4,959,314 | 9/1990 | Mark et al. | 435/172.3 |
| 5,017,692 | 5/1991 | Zurawski et al. | 530/351 |
| 5,047,505 | 9/1991 | Huang | 435/69.52 |
| 5,211,946 | 5/1993 | Wallach et al. | 424/85.1 |
| 5,376,639 | 12/1994 | Yamada et al. | 424/85.2 |
| 5,510,462 | 4/1996 | Cheron et al. | 424/85.2 |
| 5,543,140 | 8/1996 | Nakai et al. | 424/85.2 |

OTHER PUBLICATIONS

March et al., "Cloning, Sequence and Expression of Two Distinct Human Interleukin–1 Complementary DNAs", *Nature*, 315(6021):641–647 (1985).

Wells et al., "Cassette Mutagenesis: An Efficient Method for Generation of Multiple Mutations at Defined Sites", *Gene*, 34:615–323 (1985).

Sato et al., "Recombinant Interleukin 1 Alpha and Beta Stimulate . . . ", *Biochem. Biophys. Res. Comm.*, 141(1):285–291 (Nov. 1986).

Onazaki et al., "Human Interleukin 1 is a Cytocidal Factor for Several Tumor Cell Lines", *J. Immunol.* 135(6):3962–3968 (Dec. 1985).

Nakamura et al., "Antitumor Effect of Recombinant Human Interleukin 1 Alpha Against Murine Syngenic Tumors", *Jpn. J. Cancer Res.*, 77:767–773 (Aug. 1986).

Chu et al., "Role of Interleukin 1 in Antigen–Specific T Cell Proliferation", *J. Immunol.*, 132(3):1311–1316 (Mar. 1984).

Gaffney et al "Inhibition of Cell Growth by Interleukin 1 (IL–1)" *Proc. Am. Assoc. Can. Res.* 26:269, Abstract #1058 (Mar. 1985).

Matsushima et al, pp. 253–262 in *The Physiologic, Metabolic and Immunologic Actions of Interleukin–1*, (Alan R. Liss, Inc., NY, 1985).

Herman et al., "The Role of Interleukin 1 (IL 1) in Tumor–NK Cell Interactions . . . " *J. Immunol.* 135(4):2882–2886 (Oct. 1985).

(List continued on next page.)

*Primary Examiner*—Garnette D. Draper
*Attorney, Agent, or Firm*—Sughrue,Mion,Zinn,Macpeak & Seas, PLLC

[57] ABSTRACT

Methods are disclosed for promoting production of colony stimulating factor and inhibiting growth of Meth A tumor cells comprising administering a pharmaceutically effective amount of modified IL-1α to a subject.

1 Claim, 8 Drawing Sheets

OTHER PUBLICATIONS

Lachman et al "Natural and Recombinant Human Interleukin 1-β is Cytotoxic . . . ", *J. Immunol.* 136(8):3098–3102 (Apr. 1986).

Onozaki et al, "Role of Interleukin 1 in Promoting . . . Tumor Cytotoxicity" *J. Immunol.* 135(1):314–320 (Ju. 1985).

Zucali et al, "Interleukin 1 Stimulates Fibroblasts . . . " *J. Clin. Invest.* 77:1857–1863 (Jun. 1986).

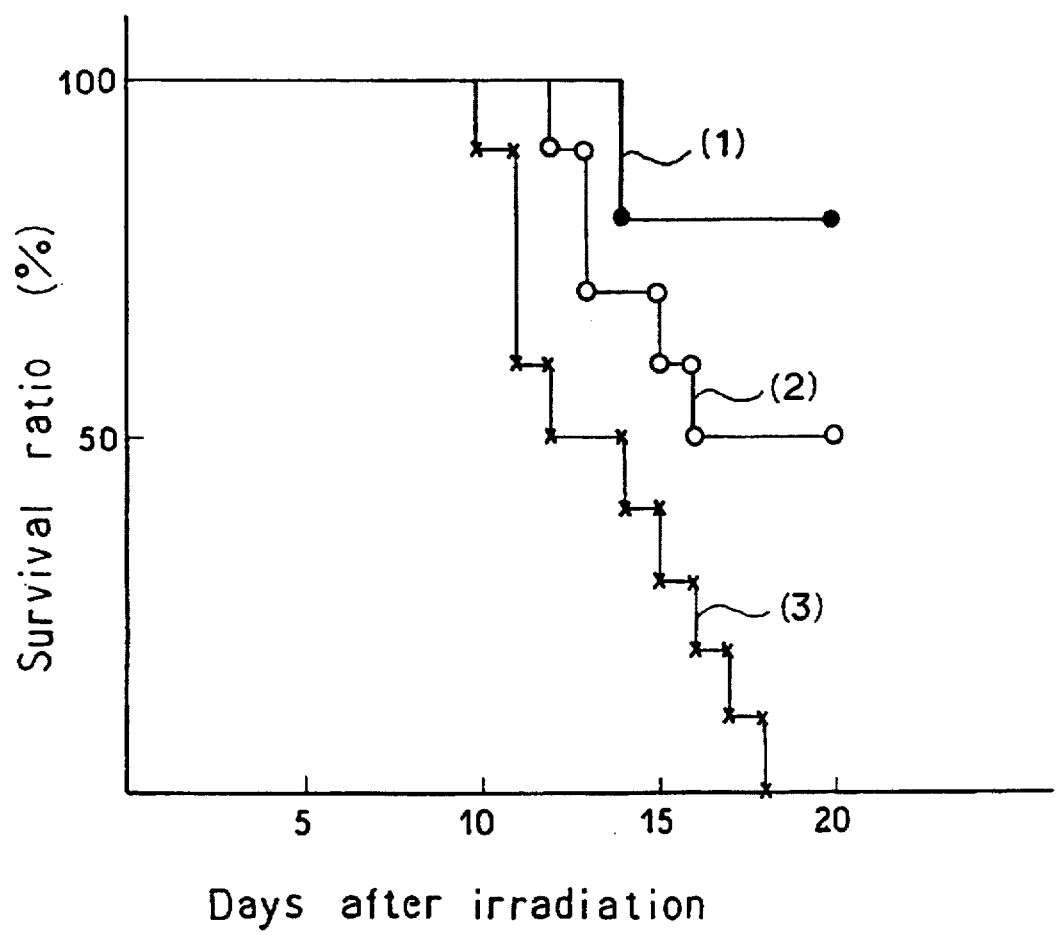

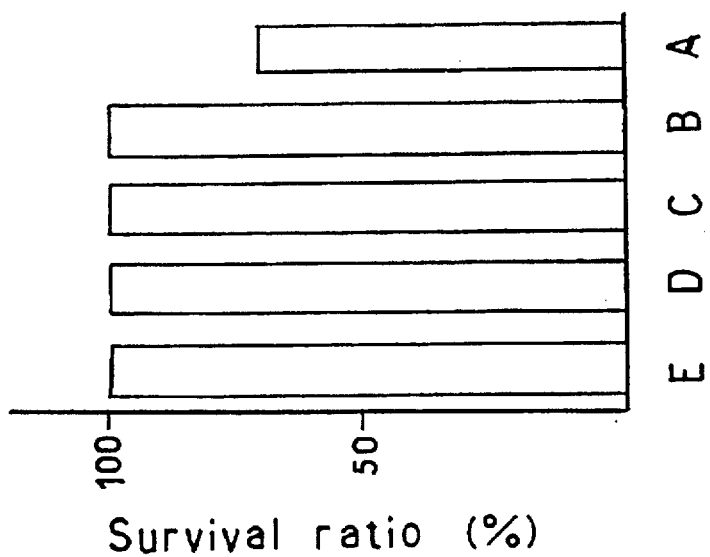
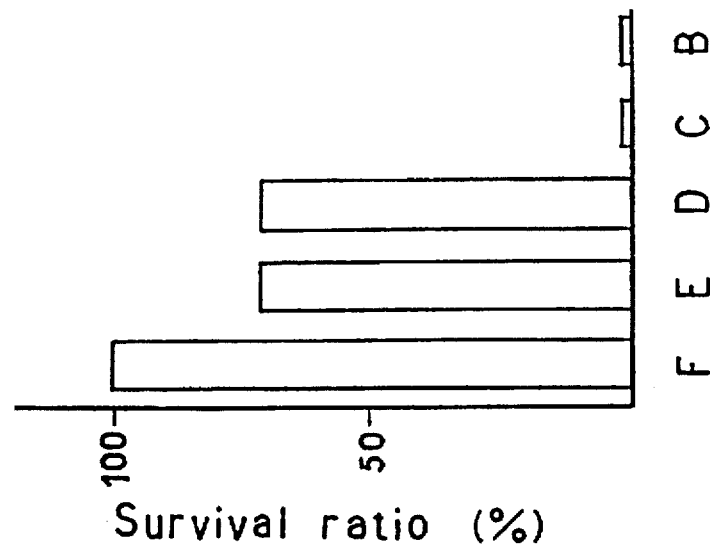
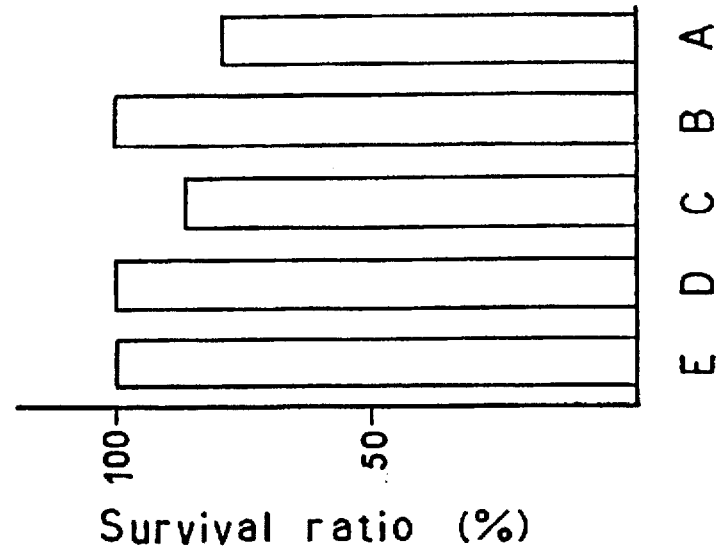

METHODS OF USE OF IL-1α

This is a Divisional Application of application Ser. No. 08/252,229, filed Jun. 1, 1994, now U.S. Pat. No. 5,543,140, which is a Divisional Application of application Ser. No. 07/643,292 filed Jan. 22, 1991, now U.S. Pat. No. 5,371,204; which is a Divisional of U.S. application Ser. No. 07/023,373 filed Mar. 9, 1987, now U.S. Pat. No. 5,008,374.

The present invention relates to novel polypeptides, and more particularly to novel derivatives of interleukin-1α (IL-1α) and to the medicinal use of IL-1α and the novel derivatives thereof.

The Second International Lymphokine Workship decided to adopt a unified name, interleukin-1 (IL-1), for the physiologically active substances which had been referred to as lymphocyte activating factor (LAF), mitogenic protein, helper peak-1, T-cell replacing factor III (TRF-III), T-cell replacing factor Mφ (TRFM), B-cell activating factor, B-cell differentiation factor, etc. (Cellular Immunol., 48, 433–436 (1979)). This decision is based on the reason that these physiologically active substances can not be distinguished from one another as different substances but are expressed variously merely with reference to physiological activities as interpreted from different angles.

Further it is reported that IL-1 activates T lymphocytes and B lymphocytes, has activity to promote production of interleukin-2 and antibodies, acts on liver tissues to promote protein synthesis and possesses activity to promote production of prostaglandins (see Reviews of Infectious Disease, Vol. 6, No. 1, 51–59 (1984), New England J. of Med., 311, 1413 (1984), etc.).

Whereas IL-1 itself still remains to be clarified as a substance, it is only recently that reports are made on the presence of genes coding for polypeptides having LAF activity or precursor thereof (Proc. Natl. Acad. Sci., Vol. 81, 7907–7911 (1984), Nature, Vol. 315, 641 (1985), Nucleic Acid Research, Vol. 13 (16), 5869 (1985)).

According to the report, a culture supernatant obtained by gene recombination techniques was found to have LAF activity, and based on this finding, it is speculated that the polypeptide represented by the following formula (A) is a polypeptide having LAF activity and is termed "IL-1α."

```
              5                          10           (A)
Ser—Ala—Pro—Phe—Ser—Phe—Leu—Ser—Asn—Val—
              15                         20
Lys—Tyr—Asn—Phe—Met—Arg—Ile—Ile—Lys—Tyr—
              25                         30
Glu—Phe—Ile—Leu—Asn—Asp—Ala—Leu—Asn—Gln—
              35                         40
Ser—Ile—Ile—Arg—Ala—Asn—Asp—Gln—Try—Leu—
              45                         50
Thr—Ala—Ala—Ala—Leu—His—Asn—Leu—Asp—Glu—
              55                         60
Ala—Val—Lys—Phe—Asp—Met—Gly—Ala—Tyr—Lys—
              65                         70
Ser—Ser—Lys—Asp—Asp—Ala—Lys—Ile—Thr—Val—
              75                         80
Ile—Leu—Arg—Ile—Ser—Lys—Thr—Gln—Leu—Tyr—
              85                         90
Val—Thr—Ala—Gln—Asp—Glu—Asp—Gln—Pro—Val—
              95                         100
Leu—Leu—Lys—Glu—Met—Pro—Glu—Ile—Pro—Lys—
              105                        110
Thr—Ile—Thr—Gly—Ser—Glu—Thr—Asn—Leu—Leu—
              115                        120
Phe—Phe—Trp—Glu—Thr—His—Gly—Thr—Lys—Asn—
              125                        130
Tyr—Phe—Thr—Ser—Val—Ala—His—Pro—Asn—Leu—
              135                        140
Phe—Ile—Ala—Thr—Lys—Gln—Asp—Tyr—Trp—Val—
              145                        150
Cys—Leu—Ala—Gly—Gly—Pro—Pro—Ser—Ile—Thr—
              155
Asp — Phe — Gln — Ile — Leu — Glu — Asn — Gln — Ala
```

However, no reports have been made to the effect that the above active substance, as well as the physiologically active substance which is reportedly known as the so-called IL-1, is prepared and isolated as a homogeneous substance, nor has there been any report on the physiological activity of such a homogeneous substance.

We conducted intensive research on IL-1α as a homogeneous substance and already established a technique for preparing this substance and clarified the characteristics, physiological activity, etc. thereof. Based on the results of the research, we also confirmed that the polypeptide of the foregoing formula (A) has LAF activity.

Nevertheless, we have found the surprising fact that the polypeptide, although corresponding to a gene of the living body as reported, is unstable as a substance.

Accordingly, an object of the present invention is to provide a novel polypeptide (IL-1α derivative) which differs from the polypeptide of the formula (A) in amino acid sequence, is more stable as a substance and has suitable characteristics for medicinal uses.

Another object of the present invention is to provide a novel medicinal composition comprising the IL-1α derivative.

The present invention provides a gene coding for a novel IL-1α derivative and a process for preparing the IL-1α derivative, i.e. polypeptide, by gene engineering techniques using the gene.

Further the present invention is to provide a novel medicinal use of IL-1α itself.

More specifically, the present invention provides a polypeptide having a modified amino acid sequence of interleukin-1α represented by the foregoing formula (A) wherein at least one amino acid residue selected from among Asn at the 36 position and Cys at the 141 position is deficient or replaced by another amino acid.

Amino acids and polypeptide are herein referred to by symbols according to the nomenclature or the rules recommended by IUPAC and IUPAC-IUB or by symbols conventionally used in the art. The nucleic acids in base sequences are also similarly expressed.

The IL-1α derivatives of the present invention have, physiological activities such as LAF activity, activity to inhibit growth of tumor cells (GIF activity), i.e. activity to specifically inhibit growth of tumor cells, activity to promote production of various cytokines such as colony stimulating factor (CSF), interferon (IFN), interleukin-2 (IL-2) and interleukin-3 (IL-3), i.e. activity for example on human cells to greatly promote production of such cytokines, anti-inflammatory activity, i.e., activity for example to effectively inhibit progress of arthritis, when administered to model animals with arthritis, and activity to prevent radiation injury, i.e. activity to prevent the possible living body disorders or serious side effects that would result from systemic radiation irradiation during bone marrow transplant, radiation irradiation for treatment of cancers and radiation accident. Accordingly, the present derivatives are very useful as immune system stimulants, for example, for promoting production of antibodies and enhancing the effect of vaccines, antitumor agents, agents for promoting production of cytokines such as CSF, IFN, IL-2 and IL-3, anti-inflammatory agents, agents for preventing radiation injury and other like medicinal agents. Especially, the polypeptide of the present invention has the feature of being an exceedingly stable substance and is low in toxicity. Further, IL-1 is known as being pyrogenetic whereas the polypeptide of the present invention is excellent in being low in such side effect.

The derivatives of the invention are effective especially as CSF production promoting agents. For example, when administered to man, the derivative effectively cures granulocytopenia due to impaired formation of bone marrow resulting from chemotherapy or radiation therapy for cancers without entailing the likelihood of virus infections or antigen-antibody reaction (granulocytopenia curing drug). The CSF production promoting agent is usable also for preventing and curing various diseases owing to the activity of CSF the production of which is promoted by the agent as contemplated. For example, CSF acts to promote the function of granulocytes and macrophages (Lopez, A. F. et al., J. Immunol., 131, 2983 (1983); Handam, E. et al., same, 122, 1134 (1979) and Vadas, M. A. et al., same, 130, 795 (1983)), so that clinical application is expected of CSF for preventing and curing various infections. Similarly, the CSF production promoting agent is expected to be useful for clinical application.

In recent years, it is noted that compromised hosts with impaired biophylactic ability suffer from so-called opportunistic infections or terminal infections which occur when harmless pathogens become pathogenic. Clinically, these infections are attributable to pathogens including gram-negative bacilli such as Pseudomonas and Serratia, viruses such as Herpes simplex virus (HSV), Varicella-zoster virus (VZV) and Cytomegalovirus (CMV), fungi such as *candida albicans*, *Aspergillus fumigatus* and *nocardia asteroidea*, protozoa such as *Pneumocystis carinii* and *Toxoplasma gondii*, etc. Since the antibiotics presently used are not fully effective on the opportunistic infections, it is desired to conduct research on and develop new drugs for such infections. The present derivatives are effective also for preventing and curing opportunistic infections which occur frequently especially when anticancer drugs are given. For example, they are useful for preventing and curing various infections which develop during chemotherapy of acute leukemia and bone marrow transplant, such as candidosis, cryptococcosis, aspergillosis, zygomycosis, chromomycosis, virus infections, Cytomegalovirus pneumonia and complications of these infections.

Further, the polypeptide of the present invention is effective in preventing and curing arthritis or the like and therefor useful as anti-inflammatory agent.

The polypeptide of the present invention has activity to inhibit growth of tumor cells (hereinafter referred to as "GIF activity") as determined by the method described in the example to follow, acting specifically on various tumor cells to inhibit the growth thereof. Accordingly, the antitumor composition comprising the present polypeptide as its active component is advantageously usable as a chemotherapeutic agent for cancers, especially in combination with various agents for treating malignant tumors for a fortified remission therapy and remission maintaining therapy.

Moreover, in addition to the foregoing therapeutic purposes, the polypeptide of the present invention can be effectively used, for example, in preparing useful cytokines in vitro from cell strain due to the activity to promote the production of cyctokines. Attention is focussed on the manufacture of glycoprotein-type cytokines among natural cytokines produced from cell strain. Useful cytokines can be produced in large quantities with efficiency.

Our research discovered novel biological activities of IL-1α. The IL-1α of the invention has GIF activity and activity to promote the production of CSF, and can be used for said various therapeutic purposes due to these biological activities.

Among the polypeptides of the invention preferable are those having the amino acid sequence represented by the formula (A) wherein at least Asn at the 36 position is deficient or replaced by another amino acid. The amino acid capable of replacing Asn at the 36 position and Cys at the 141 position can be the residue of any of α-amino acids constituting living body proteins. However, in view that Cys is likely to form an inter- or intra-molecular linkage due to the presence of SH group thereof, preferred amino acids are those other than Cys. Particularly, Asp is preferable for replacing Asn at the 36 position and Ser is preferable for replacing Cys at the 141 position.

The polypeptides of the present invention can be prepared, for example, by gene engineering techniques using a gene coding for the specific polypeptide of the invention, i.e., by incorporating the gene into a micro-organism vector to effect replication, transcription and translation within the cell of the microorganism. This process is advantageous in that it is amenable to mass production.

Although the gene to be used in this process can be totally synthesized through chemical synthesis of nucleic acids by a usual method, for example, by the phosphite triester method (Nature, 310, 105 (1984)) or the like, it is convenient to utilize the gene coding for IL-1α or a precursor thereof. By a conventional method involving the above chemical synthesis, the gene is modified to a sequence of nucleic acids coding for the foregoing specific amino acid sequence, whereby the desired gene can be prepared easily.

The gene coding for IL-1α or a precursor thereof is already known. We obtained the gene coding for IL-1α and succeeded in preparing IL-1α by gene engineering techniques using this gene. The series of gene engineering techniques employed will be described in the reference examples to follow.

The above-mentioned modified sequence of nucleic acids (bases) is prepared also by a known procedure, which executed according to the amino acid sequence of the desired polypeptide (Molecular Cloning, Cold Spring Harbor Laboratory (1982)).

For example, cleavage, ligation, phosphorylation, etc. of DNA can be carried out by usual methods including treatment with enzymes such as restriction enzymes, DNA ligase, polynucleotidekinase and DNA polymerase, which are readily available as commercial products. The isolation and purification of the gene and nucleic acids included in these methods are conducted also in the usual manner, for example, by agarose gel electrophoresis. As will be described partially later, the gene obtained is replicated using a usual vector. The DNA fragment coding for the desired amino acid sequence and synthetic linkers can be prepared also easily by the above-mentioned chemical synthesis. The codon corresponding to the desired amino acid and to be used in the above methods is known and is selected as desired. A usual method may be used for this purpose, for example, in view of the frequency of use of the codon of the host to be used (Nucl. Acids Res., 9, 43–74 (1981)). Further for the modification of the codon in the nucleic acid sequence concerned, for example, site-specific mutagenesis (Proc. Natl. Acad. Sci., 81, 5662–5666 (1984)) can be resorted to as usually done which employs a primer comprising a synthetic oligonucleotide coding for the desired modified sequence about 15–30 mer.

The desired gene obtained by the foregoing process can be checked for its base sequence, for example, by the Maxam-Gilbert chemical modification method (Meth. Enzym., 65, 499–560 (1980) or by the dideoxynucleotide chain termination method using M13 Phage (Messing, J. and Vieira, J., Gene, 19, 269–276 (1982).

While the above process and procedures therefor will be described in the reference examples and examples to follow, the process is not specifically limited; any process already known in the art may be used.

Thus, the present invention also provides a novel gene coding for a polypeptide having the above-specified amino acid sequence. (The gene will hereinafter be referred to as the "present gene.")

The polypeptide of the present invention can be prepared by usual known gene recombination techniques using the present gene. More specifically, it is produced by preparing a recombinant DNA which can express the present gene in host cells, transforming the DNA into the host cell and incubating the transformant.

Useful host cells can be either eucaryotic or procaryotic cells. The eucaryotic cells include cells of vertebrate animals, yeasts, etc. Generally used as cells of vertebrate animals are, for example, COS cells which are cells of monkey (Y. Gluzman, Cell, 23, 175–182 (1981), dihydrofolate acid reductase defective strain of Chinese hamster ovary cell (G. Urlaub and L. A., Chasin, Proc. Natl. Acad. Sci., U.S.A., 77, 4216–4220 (1980), etc., while useful cells are not limited to these cells. Useful expression vectors of vertebrate cells are those having a promotor positioned upstream of the gene to be expressed, RNA splicing sites, polyadenylation site, transcription termination sequence, etc. These vectors may further have a replication origin when required. Examples of useful expression vectors include pSV2dhfr having an initial promotor of SV40 (S. Subramani, R. Mulligan and P. Berg, Mol. Cell. Biol., 1(9), 854–864), which is not limitative.

Yeasts are widely used as eucaryotic micro-organisms, among which those of the genus Saccharomyces are generally usable. Examples of popular expression vectors of yeasts and like eucaryotic microorganisms include pAM82 having a promotor for acid phosphatase gene (A. Miyanohara et al., Proc. Natl. Acad. Sci., U.S.A., 80, 1–5 (1983), etc.

E. coli and Bacillus subtilis are generally used as procaryotic hosts. The present invention employs, for example plasmid vectors capable of replication in the host. To express the gene in the vector, expression plasmids can be used which have a promotor and SD (Shine-Dalgarno) base sequence at the upstream of the gene and ATG required for initiating protein synthesis. Widely used as host E. coli is E. coli K12 strain. pBR322 is a vector which is generally used. However, these are not limitative, and various known strains and vectors are usable. Examples of promotors usable are tryptophan promotor, $P_{L\ m}$ promotor, lac promotor, lpp promotor, etc. The gene can be expressed with use of any of these promotors.

To describe the procedure with reference to the case wherein tryptophan promotor is used, vector pTM1 (Fumio Imamoto, Taisha (Metabolism), Vol. 22, 289 (1985) having tryptophan promotor and SD sequence is used as an expression vector. A gene coding for a desired polypeptide of this invention and having ATG when required is linked to the site of restriction enzyme ClaI which is present downstream from the SD sequence.

Incidentally, not only the direct expression system but a fusion protein expression system is also usable which employs, for example, β-galactosidase, β-lactamase or the like.

The expression vector thus obtained is introduced into host cells and thereby transformed by usual methods. For example, cells chiefly in the logarithmic growth phase are collected, treated with $CaCl_2$ and thereby made to readily accept DNA, whereupon the vector is introducted into the cell. With this method, $MgCl_2$ or RbCl can be made present conjointly with the vector so as to achieve an improved transformation efficiency, as is generally known. The cell can be converted to spheroplast or protoplast before transformation.

The desired transformant thus obtained can be incubated in the usual manner, whereby the desired polypeptide is produced and accumulated. The medium for the incubation may be any of those generally used for incubating cells, such as L medium, E medium, M9 medium, etc. Various carbon sources, nitrogen sources, inorganic salts, vitamins, etc. which are usually known can be admixed with these media. When the tryptophan promotor is used, M9 minimum medium, for example, is usable which has usually admixed therewith Casamino acid for effecting the action of the promotor. A chemical, such as indoleacrylic acid, for enhancing the action of tryptophan promotor can be added to the medium at a suitable stage of incubation.

The desired polypeptide of the present invention can be isolated from the resulting culture and purified by usual methods. It is desirable to extract the polypeptide from the host under a mild condition as by osmotic shock in order to maintain the higher order structure thereof.

The above isolation or purification method is conducted substantially by the same method as usually used for separating a protein-like substance from such a biological substance. For example, various procedures are usable utilizing the physical or chemical properties of the desired polypeptide. (See for example, "Biological Data Book II," pp. 1175–1259, 1st edition, 1st print, Jun. 23, 1980, published by Kabushiki Kaisha Tokyo Kagakudojin.) Examples of useful procedures are treatment with use of a usual protein precipitating agent, ultra-filtration, molecular sieve chromatography (gel filtration), liquid chromatography, centrifugation, electrophoresis, affinity chromatography, dialysis, and combinations of such procedures.

The desired polypeptide is separated from the supernatant as partially purified. This partial purification is carried out, for example, by a treatment using as a protein precipitating agent an organic solvent such as acetone, methanol, ethanol, propanol or dimethylformamide (DMF), or an acidic reagent such as acetic acid, perchloric acid (PCA) or trichloroacetic acid (TCA), a treatment using a salting-out agent such as ammonium sulfate, sodium sulfate or sodium phosphate and/or ultrafiltration using a dialysis membrane, flat membrane, hollow fiber membrane or the like. These treatments are conducuted in the same manner as usually done under usual conditions.

The roughly purified product thus obtained is then subjected to gel filtration, whereby a fraction exhibiting the activity of the desired substance is collected. Useful gel filtration agents are not limited specifically. Such agents include those made of dextran gel, polyacrylamide gel, agarose gel, polyacrylamide-agarose gel, cellulose or the like. Examples of useful agents commercially available are Sephadex G type, Sephadex LH type, Sepharose type, Sephacryl type (all products of Pharmacia Fine Chemicals AB), Cellofine (Chisso Corporation), Biogel P type, Biogel A type (both product of Bio-Rad Laboratories), Ultro gel (LKB Producter AB), TSK-G type (product of Toyo Soda Mfg. Co., Ltd.), etc.

The polypeptide of the present invention can be isolated from the fraction as a homogeneous substance, for example, by subjecting the fraction to affinity chromatography with use of a hydroxyapatite column, ion exchange column chromatography as of the DEAE, CM or SP method, chromatofocusing method, reverse-phase high-performance liquid chromatography or the like, or to a combination of such methods.

The chromatofocusing method can be carried out by various known procedures. Usable as the column is, for example, PBE94 (Pharmacia) or the like, as the starting buffer, for example, imidazole-hydrochloric acid or the like, and the eluent, for example, the mixture of Polybuffer 74 (Pharmacia) and hydrochloric acid (pH 4.0) or the like.

The reverse-phase high-performance liquid chromatography can be conducted, for example, with $C_4$ Hi-Pore reverse-phase HPLC column (Bio-Rad Laboratories) or the like, using acetonitrile, trifluoroacetic acid (TFA), water or the like, or a mixture of such solvents as the eluent.

In this way, the IL-1α derivative (polypeptide) of the present invention can be obtained upon isolation. The gene coding for IL-1α affords IL-1α through a similar gene recombination procedure.

The IL-1α and derivatives thereof of the invention, which have outstanding pharmacological activities as already stated, can be formulated into useful preparations for the afore-mentioned medicinal uses. Examples of such medicinal preparations include immunostimulators for producing antibodies, enhancing the effect of vaccines and curing immunodeficiency, antitumor agents, cytokine production promotors, anti-inflammatory agents, agents for preventing or curing radiation sickness, agents for preventing or curing opportunistic infections, etc. These medicinal preparations are formulated usually in the form of pharmaceutical compositions comprising a pharmacologically effective amount of the IL-1α or derivative thereof of the present invention and a suitable carrier. Examples of useful pharmaceutical carriers include excipients and diluents such as filler, extender, binder, wetting agent, disintegrator, surfactant, etc. which are generally used for preparing pharmaceuticals of the desired form to be used. The form of the pharmaceutical compositions is not specifically limited insofar as they effectively contain the present polypeptide or IL-1α but can be, for example, in the form of tablets, power, granules, pellets or like solid preparation. Usually, however, it is suitable that the composition be in the form of a solution, suspension, emulsion or the like for injection. Alternatively, such a composition can be a dry product which can be made liquid with addition of a suitable carrier before use. The pharmaceutical compositions mentioned above can be prepared by usual methods.

In accordance with the form of the pharmaceutical composition obtained, the composition is administered via a suitable route. For example, those for injection are given intravenously, intramuscularly, subcutaneously, intracuteneously, intraperitoneally or otherwise. The solid composition is given orally or intraintestinalty. The amount of the active component of the composition and the dosage of the composition are suitably determined according to the method and form of administration, purpose of use, symptoms of the patient, etc. and are not definitely determinable. It is generally desirable to incorporate about 1 to about 80 wt. % of the active component into the pharmaceutical preparation and to give the preparation at a daily dose of about 0.1 μg to about 10 mg, calculated as the active component, for adults. The preparation need not always be given only once a day but can be given in three to four divided doses daily.

The present invention will be described in greater detail with reference to the following examples.

In the following examples, physiological activities were determined by the following methods.

(1) Determination of IL-1 activity

Expressed in terms of LAF activity as measured by the method of J. J. Oppenhein et al. (J. Immunol., 116, 1466 (1976) using thymus cells of a mouse of C3H/HeJ strain.

(2) Determination of GIF activity

Portions (0.1 ml) of the test solution diluted to varying concentrations were placed into the wells of 96-well microplate (Corning Glass Works), 0.1 ml of Eagle's MEM suspension containing 10% FCS containing human melonoma cells A375 in an amount of $2 \times 10^4$ cells/ml was then placed into each well, and the cells were incubated in a $CO_2$ incubator (Napco Co., Ltd.) for 4 days. After the incubation, 0.05 ml of 0.05% Neutral Red (Wako Pure Chemical Ind. Ltd.) was placed into each well, followed by incubation at 37° C. for 2 hours. After removing the supernatant, 0.3 ml of phosphoric acid buffer saline was gently poured into each well for washing. After removing the washing, 0.1 ml of mixture of sodium phosphate monobasic and ethanol in equal amounts was placed into each well, the plate was shaken for several minutes by a micromixer, and the amount of pigment taken into the cell was measured at an absorbance of 540 mμ using a photometer for 96-well microtitration plates (Titer check multiscane, Flow Lab.) to determine growth inhibition activity. The test group exhibiting 50% of the inhibition of cell growth of the control group, i.e., the test group which exhibited ½ the absorbance measured of the control group, was identified. The reciprocal of the number of times of dilution for the test group was taken as the GIF activity unit. Accordingly, when the GIF activity is 10 units, for example, the test solution, if diluted tenfold, still has activity to inhibit cell growth 50%.

The following drawings are referred to in reference examples and examples.

BRIEF DESCRIPTION OF THE DRAWINGS

FIG. 7 shows the results obtained by testing the polypeptide of the invention for activity to prevent radiation injury; and FIGS. 8(a), (b) and (c) show the results obtained by testing the polypeptide of the invention for activity to prevent opportunistic infection.

REFERENCE EXAMPLE 1

(1) Incubation of U937 cells

Figure 1:
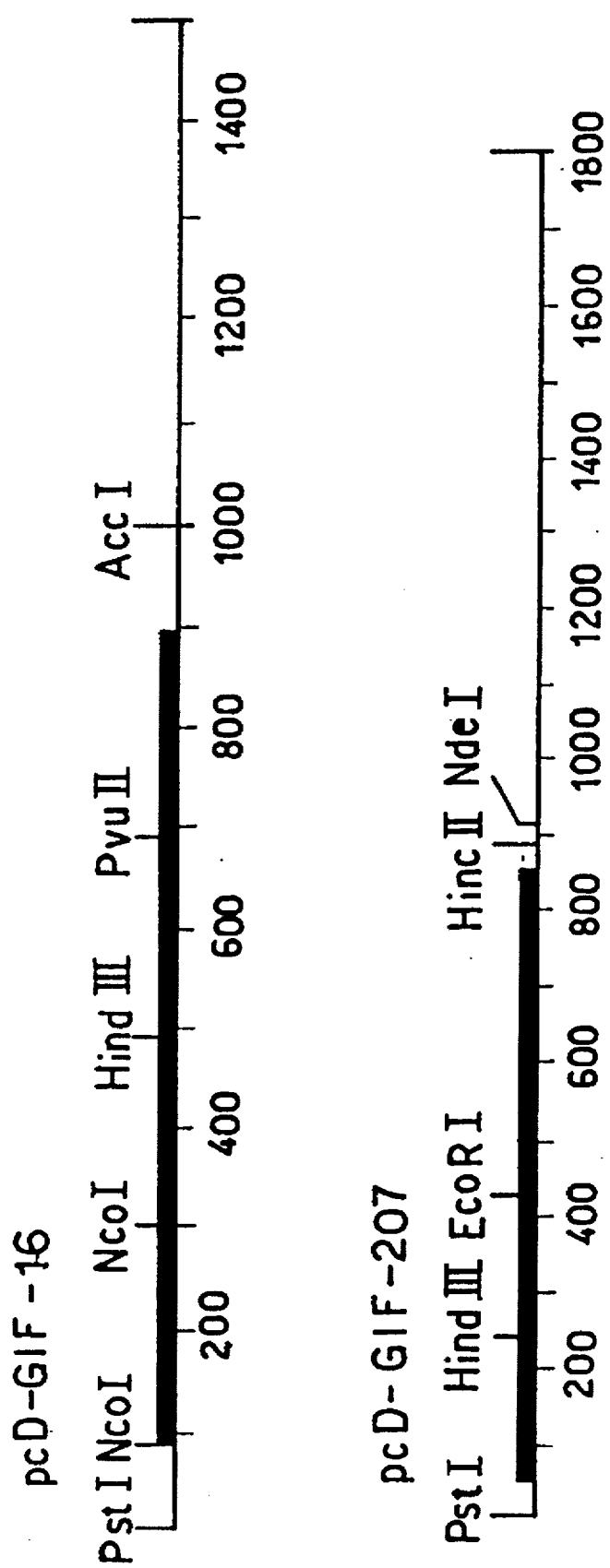
FIG. 1(a) shows a restriction enzyme map of cDNA of plasmid pcd-GIF-16.
FIG. 1(b) shows a restriction enzyme map of cDNA of plasmid pco-GIF-207.

Human histiocytic lymphoma U937 cells (Ascenso, J. L. et al., Blood, Vol. 57, p170 (1981), $1.4 \times 10^9$ in number, were placed into RPMI-1640 culture medium containing 25 ng/ml of 12-o-tetradecanoylphorbol-13-acetate (TPA, product of Pharmacia), 10 µg/ml of concanavalin A (ConA, product of Sigma Chemical Co.) and 10% FCS to prepare a cell suspension having a concentration of $4 \times 10^5$ cells/ml.

Ten-ml portions of the cell suspension were separately placed into dishes (Falcon 3003), 9 cm in diameter, and incubated in 5% carbon dioxide gas at 37° C. for 3 days. After removing the culture supernatant by an aspirator, 10 ml of RPMI-1640 medium containing 10% FCS, 10 µg/ml of bacterial lipopolysaccharide (LPS, product of Difco), 1 µg/ml of muramyldipeptide (MDP, product of Wako Pure Chemical Ind. Ltd.) and 1 ng/ml of TPA was placed into each dish. The cells were incubated in this medium in 5% carbon dioxide gas at 37° C. for 18 hours. The U937 cells adhering to the bottom of the dish were used for preparing mRNA.

(2) Preparation of mRNA

RNA was extracted by the combination of the guanidinium/hot phenol method (Feramisco, J. R. et al., J. Bio. Chem., Vol. 257, 11024 (1982) and the guanidinium/cesium chloride method (Glisin, V, et al., Biochemistry, Vol. 13, 2633 (1974).

To wash the U937 cells incubated by the procedure (1), the dishes were rinsed with 5 ml of PBS(−) solution after removing the supernatant. The cells were then dissolved with 1 ml of 4M guanidine isothiocyanate solution (4M guanidine isothiocyanate (product of Fluka AG.), 50 mM tris-HCl (pH 7.6), 10 mM EDTA and 2% sodium lauroyl sarkosinate placed into each dish. The solution was collected with rubber polisher and Pasteur pipette to obtain 420 ml of cell solution, which was maintained at 60° C. and passed through 18G injection needle to shear the chromosome DNA. Subsequently, phenol heated to 60° C. was added to the solution in an amount equal to that of the solution, and the mixture was stirred with 18G injection needle for further shearing. To the mixture were then added 210 ml of 0.1M sodium acetate-10 mM tris-HCl (pH 7.4)-1 mM EDTA solution and 420 ml of chloroform:isoamyl alcohol mixture (24:1 in volume ratio). The resulting mixture was vigorously agitated at 60° C. for 15 minutes, then ice-cooled and centrifuged at 3000 r.p.m. at 4° C. for 20 minutes. To the aqueous layer collected was added ethanol in two times the amount of the aqueous layer. The mixture was allowed to stand overnight at −70° C. to obtain crude RNA precipitate. The crude RNA was dissolved in 48 ml of 6M guanidine isothiocyanate-5 mM sodium citrate (pH 7.0)-0.1M β-mercaptoethanol-0.5% sodium lauroyl sarkosinate solution. Cesium chloride (19.2 g) was then dissolved in the solution. Seven-ml portions of the resulting solution was then superposed on 4 ml of 5.7M cesium chloride-0.1M EDTA (pH 7.5). The mixture was centrifuged at 31500 r.p.m. at 25° C. for 20 hours by Beckman SW40Ti rotor to collect RNA.

Thus, 9.7 mg of RNA was obtained.

To obtain mRNA from the RNA, the RNA was subjected to column chromatography using oligo(dT)-cellulose (product of Collaborative Research Inc.). For adsorption, 10 mM tris-HCl (pH 7.5)-0.5M NaCl-1 mM EDTA was used. For elution, 10 mM tris-HCl (pH 7.5)-1 mM EDTA was used.

Consequently, 400 µg of mRNA was obtained.

(3) Preparation of cDNA library cDNA library was prepared by the Okayama-Berg method by which cDNA can be expressed in animal cells. Thus, dT tail-attached vector primer for use in cDNA cloning was prepared from plasmid pcDV1, and dG tail-attached linker DNA from plasmid pL1, each by the method of Okayama et al. (Okayama, H. and P. Berg, Molecular and Cellular Biology, Vol. 3, p. 280 (1983).

mRNA (15 µg) obtained by the procedure (2) was dissolved in 20 µl of 5 mM tris-HCl (pH 7.5)-0.5 mM EDTA (pH. 7.5) aqueous solution and incubated at 65° C. for 5 minutes and then at 37° C. for 5 minutes. The reaction mixture was adjusted to a total quantity of 40 µl containing 50 mM tris-HCl (pH 8.3), 8 mM $MgCl_2$, 30 mM KCl, 0.3 mM dithiothreitol, 2 mM of each of dATP, dGTP, dCTP and dTTP, 2.8 µg of vector primer DNA, 60 units of RNase inhibitor (product of Promega Biotech) and 40 units of reverse transferase (product of Bio-Rad), followed by incubation at 37° C. for 1 hour. The reaction was terminated by addition of 2 µl of 0.5M EDTA (pH 7.5) and 2 µl of 10% SDS. Subsequently, the mixture was subjected to phenol-chloroform extraction and chloroform extraction, and the extract was precipitated from ethanol to collect vector primer cDNA:mRNA.

The collected vector primer cDNA:mRNA was incubated at 37° C. for 5 minutes in 30 µl of a reaction mixture composed of 140 mM sodium cacodylate, 30 mM tris-HCl (pH 6.8), 1 mM $CaCl_2$, 0.1 mM dithiothreitol, 0.3 µg of poly A, 66 µM dCTP and 38 units of terminal deoxynucleotidyl transferase (product of Pharmacia), whereupon 1.5 µl of 0.5M EDTA (pH 7.5) and 1.5 µl of 10% SDS were added to the mixture to terminate the reaction. The mixture was subjected to phenol-chloroform extraction and chloroform extraction, and the extract was precipitated from ethanol to collect oligo dC tail-attached cDNA:mRNA-vector primer.

The collected nucleic acid was incubated at 37° C. for 90 minutes in 20 µl of a reaction mixture comprising 7 mM tris-HCl (pH 7.5), 7 mM $MgCl_2$, 60 NaCl, 100 µg/ml of bovine serum albumin and 12 units of restriction enzyme HindIII (product of Nippon Gene Co., Ltd.) Subsequently, 1 µl of 0.5M EDTA (pH 7.5) and 1 µl of 10% SDS were added to the mixture to terminate the reaction, followed by extraction with phenols:chloroform and then with chloroform and by precipitation from ethanol to collect HindIII-digested oligo dC tail-attached cDNA:mRNA-vector primer. The product was dissolved in 10 µl of 10 mM tris-HCl (pH 7.5)-1 mM EDTA (pH 7.5) (TE (pH 7.5). One µl portion of the solution was incubated in 10 µl of a reaction mixture comprising the above TE (pH 7.5), 0.1M NaCl and oligo dG tail-attached linker DNA (14 ng), first at 65° C. for 2 minutes and then at 42° C. for 30 minutes. The mixture was thereafter cooled to 0° C.

The reaction mixture was adjusted to 100 µl containing 20 mM tris-HCl (pH 7.5), 4 mM $MgCl_2$, 10 mM $(NH_4)_2SO_4$, 0.1M KCl, 50 µg/ml bovine serum albumin, 0.1 mM β-NAD (nicotinamide-adenine-dinucleotide, product of Pharmacia) and 0.6 µg of *E. coli* DNA ligase (product of Pharmacia) and incubated at 12° C. overnight. To the reaction mixture were added 40 µM of each of dATP, dGTP, dCTP and dTTP and 0.15 mM of β-NAD. Further with addition of 0.4 µg of *E. coli* DNA ligase, 4.6 units of *E. coli* DNA polymerase I (product of Boehringen Mannhein) and 1 unit of *E. coli* RNase H (product of Pharmacia), the mixture was incubated at 12° C. for 1 hour and then at 25° C. for 1 hour.

*E. coli* HB101 was transformed using the reaction mixture thus obtained. The competent cells of this strain used were a product of Bethesda Research Laboratories The cells were transformed according to BRL's manual.

Consequently, cDNA library was obtained which contained about 21000 clones.

(4) Transfection of monkey COS-1 cells

The cDNA library obtained by the above procedure (3) was divided into groups each including about 70 clones on the average. Plasmid DNA was prepared from each group.

The plasmid DNA was prepared by the alkaline lysis method (Molecular Cloning-A Laboratory Manual, Cold Spring Harbor Laboratory, 1982, p. 368).

Incubated monkey cells, COS-1 cells (Gluzman, Y., Cell, Vol. 23, p. 175 (1981), were infected with the plasmid DNA thus prepared from each group for transfection. The transfection was conducted by the DEAE-dextran method (Yokota, T. et al., Proc. Natl. Acad. Sci. U.S.A., Vol. 81, p. 1070 (1984). More specifically, the COS-1 cells treated with trypsin were suspended in RPMI-1640 medium containing 10% FCS and adjusted to a concentration of $1 \times 10^6$ cells/ml. Subsequently, 500 µl portions of the suspension were placed into 6 wells of a well plate each containing 2 ml of RPMI-1640 medium containing 10% FCS. After incubating the cells at 37° C. overnight, the supernatant was removed, the cells were washed with a medium free from serum, and 1 ml of RPMI-640 medium containing 10 µg/ml of plasmid DNA, 0.4 mg/ml of DEAE-dextran (product of Pharmacia), 50 mM tris-HCl (pH 7.4) and 10% FCS was placed into each well, follwed by incubation at 37° C. for 4.5 hours. The supernatant was thereafter removed, the cells were washed with a medium free from serum and 2 ml of RPMI-1640 medium containing 150 µM chloroquine (product of Sigma) and 10% FCS was placed into each well, further followed by incubation at 37° C. for 3 hours. The supernatant was removed, and the cells were washed with a medium free from serum and thereafter incubated at 37° C. for 72 hours with addition of 3 ml of RPMI-1640 medium containing 10% FCS to the cells in each well. After collecting the supernatant, 2 ml of RPMI-1640 medium containing 10% FCS was placed into each well, followed by two freeze-thaw cycles. The cell extract was then collected. The culture supernatant and the cell extract were checked for GIF activity.

The group exhibiting GIF activity was divided into 24 groups of 10 clones each, and the same procedure as above was repeated using these groups for the determination of GIF activity. The same procedure as above was repeated for the clones within the group exhibiting GIF activity to identify the clone exhibiting GIF activity. Consequently, two kinds of clones, i.e. pcD-GIF-16 and pcD-GIF-207, were obtained.

Table 1 shows the GIF activity (GIF units/ml) of these clones.

TABLE 1

| Clone | Culture supernatant | Cell extract |
|---|---|---|
| pcD-GIF-16 | 48.3 | 120.7 |
| pcD-GIF-207 | 62.6 | 196.9 |
| pcDV1 (control) | 0 | 0 |

FIG. 1(a) shows a restriction enzyme map of cDNA of plasimid pcD-GIF-16;

FIG. 1(b) shows a restriction enzyme map of cDNA of plasimid pcD-GIF-207;

The base sequence of the cDNA of each of these plasmids was determined by the base-specific chemical modification method (Methods in Enzymology, Vol. 65, p. 499(1980) and dideoxy chain termination (Proc. Natl. Acad. Sci., U.S.A., Vol. 74, p. 5463 (1977) using phage M13 vector [Gene, Vol. 19, p. 269 (1982)].

Consequently, cDNA of pcD-GIF-207 was found identical with cDNA in the coding region of IL-1α reported by March et al. (Nature, Vol. 315, p. 641 (1985).

E. coli strain x1776 harboring plasmid pcD-GIF-207 having cDNA. coding for a precursor protein of IL-1α has been deposited under the name of "Escherichia coli χ 1776/pcD-GIF-207" with deposition number FERM BP1294 in Fermentation Research Institute, Agency of Industrial Science & Technology.

(6) Expression and preparation of polypeptide

The above plasmid, pcD-GIF-207, was cleaved with restrcition enzymes HindIII and HincII and then electrophoresed on agarose gel to isolate and purify about 0.66-kb HindIII-HincII DNA fragment, which was further cleaved with restriction enzyme AluI to similarly obtain about 0.5-kb AluI-HincII DNA fragment on isolation.

Next, synthetic oligonucleotides (5' CGATAATGTCAG-CACCTTTTAG 3' and 5' CTAAAAGGTGCTGACATTAT 3') were each phosphorylated at the 5' terminal with T4 polynucleotide kinase and ligated with AluI-HincII DNA fragment obtained above, using T4 DNA ligase. The ligated block was then cleaved with restriction enzyme ClaI and electrophoresed on agarose gel to isolate and purify about 0.54 -kb ClaI-ClaI DNA fragment.

On the other hand, plasmid pTMI (Fumio Imamoto, Taisha (Metabolism), Vol. 22, 289 (1985) was cleaved with restriction enzyme ClaI, reacted with calf intestine alkaline phosphatase (CIAP) and thereafter ligated with the approximately 0.54-kb ClaI-ClaI DNA fragment previously prepared, using T4 DNA ligase to obtain the desired polypeptide expression plasmid ptrpIL-1α-113.

This plasmid was transformed into E. coli HB101, and the desired transformant was selected by analyzing by the boiling method the size of cut-off fragments obtained from the resulting plasmid DNA.

Figure 2:
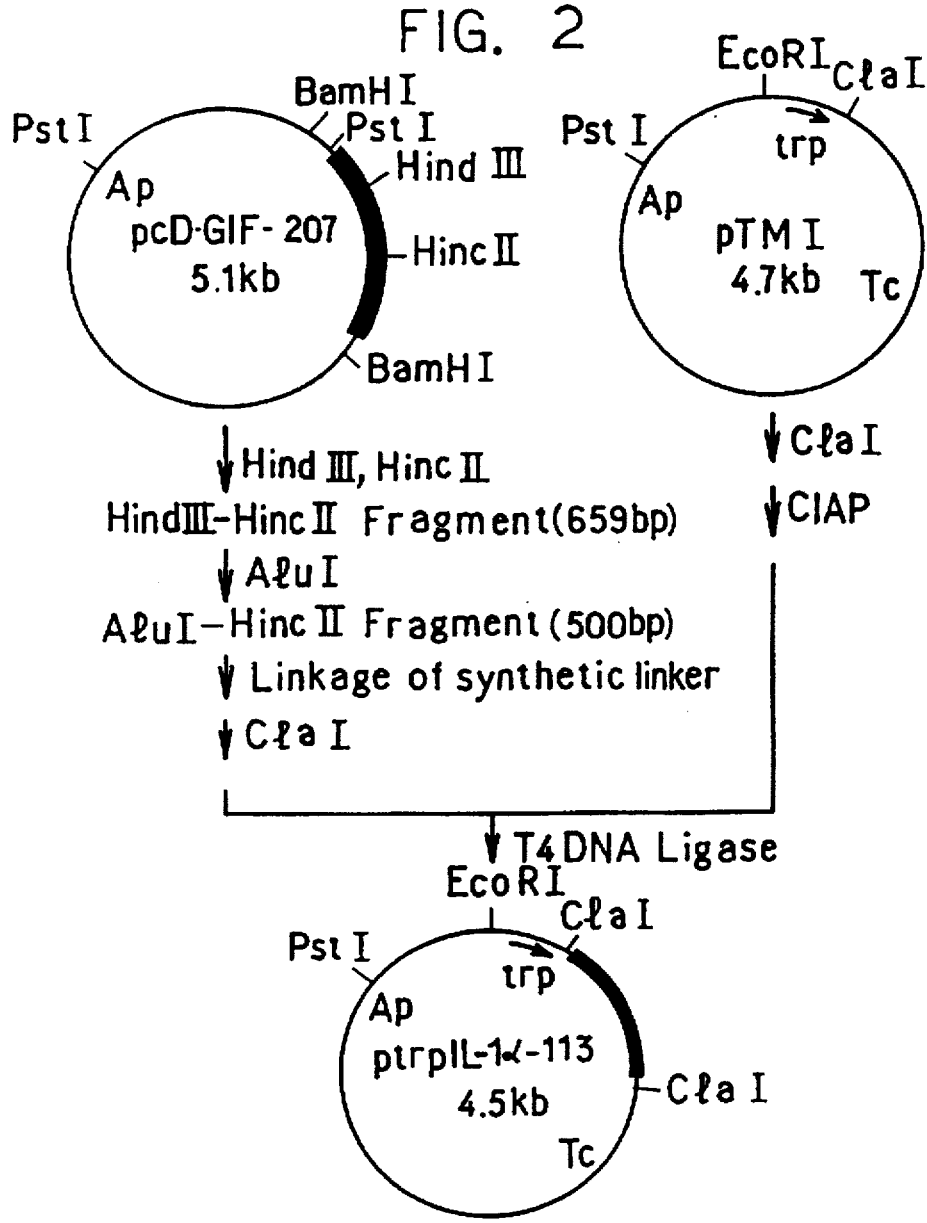
FIG. 2 is a diagram showing how plasmid ptrpIL-1α-113 is constructed from plasmid pcD-GIF-207 and plasmid pTM1.

FIG. 2 schematically shows the above procedure.

Plasmid ptrpIL-1α-113 was extracted from the selected transformant and transformed into E. coli W3110 to obtain E. coli W3110/ptrpIL-1α-113.

Example 1

(1) Incubation of transformant

The transformant (E. coli W3110/p trpIL-1α-113) obtained in Reference Example 1, (6) was incubated with shaking at 37° C. overnight in 10 ml of LB medium (1% tryptone, 0.5% yeast extract and 0.5% NaCl) containing 50 µg/ml of ampicillin and 20 µg/ml of L-tryptophan. A 400 ml quantity of M9 minimum medium (0.6% $Na_2HPO_4$, 0.3% $KH_2PO_4$, 0.05% NaCl, 0.1% $NH_4Cl$, 2 mM $MgSO_4$, 0.2% glucose and 0.1 mM $CaCl_2$) containing 50 µg/ml of ampicillin and 1% Casamino acid was inoculated with 8 ml of the culture, followed by incubation at 37° C. for 9 hours. The E. coli cells obtained were suspended in 10 ml of 1M $Na_2HPO_4$ and allowed to stand overnight in a cold chamber. The suspension was then dialyzed against 10 mM tris-HCl buffer (pH 8.0) for 2 days.

The dialyzate obtained was centrifuged and thereby separated into a supernatant and a sediment. The supernatant obtained in an amount of 28 ml was found to have GIF activity of $7.3 \times 10^7$ units.

(2) Purification of polypeptide

A 2 ml quantity of the supernatant obtained by the above procedure (1) was purified under the following conditions by ion-exchange high performance liquid chromatography (DEAE-HPLC) using ULTROCHROM GTi (LKB) chromatography system.

Column: TSK gel DEAE-5PW (7.5×75 mm, product of Toyo Soda Mfg. Co., Ltd.)
Eluent A: 20 mM tris-HCl buffer (pH 8.0)
Eluent B: 20 mM tris-HCl buffer (pH 8.0) containing 0.5M NaCl
Flow rate: 1 ml/min
Fraction volume: 1 ml/min/tube

| Gradient profile: | |
| --- | --- |
| Time (min) | % B |
| 0 | 0 |
| 5 | 0 |
| 65 | 60 |
| 70 | 100 |
| 80 | 100 |
| 85 | 0 |
| 100 | 0 |

The DEAE-HPLC procedure afforded two GIF-active fractions, i.e. a fraction of 26 to 28 min in retention time (hereinafter referred to as "fraction 1") and another fraction of 32.5 to 34.5 min in retention time (hereinafter referred to as "fraction 2").

These two fractions were subjected to DEAE-HPLC again and to gel filtration-HPLC to obtain fractions 1 and 2 as purified.

Since the divided GIF-active fractions were obtained as above, these fractions were tested as follows for confirmation.

(3) SDS polyacrylamide gel electrophoresis (SDS-PAGE)
Fractions 1 or 2 were subjected to SDS-PAGE by the method of U. K. Laemmli (Nature, 277, 680 (1970)) under the following conditions.
Specimen: Fraction 1 or 2 was completely dried, then dissolved in Laemmli sample buffer (containing 2-mercapto ethanol (2ME$^+$) in an amount of 1/20 the volume of the buffer) and treated at 100° C. for 4 minutes.
Gel: 15% Polyacrylamide gel, 1.5 mm in thickness.
Apparatus: PROTEAN, product of Bio-Rad.
Electrophoresis: 40 mA constant current for 2 hours.

The gel resulting from the electrophoresis was stained with Silver Stain Kit (Bio-Rad). Consequently, each of fractions 1 and 2 migrated as a single band at a molecular weight of about 18.3 kd, which nearly matched the molecular weight of 18 kd calculated from the gene.

(4) Isoelectrofocusing (IEF)
Fractions 1 and 2 were subjected to IEF using ampholine PAG plate (LKB), 3.5 to 9.5 in pH range, and Model 1415 (Bio-Rad) under the following conditions.
Specimens: PBS solution of fraction 1 as allowed to stand for 2 days, the same as allowed to stand for 2 weeks, PBS solution of fraction 2 as allowed to stand for 2 weeks, PBS solution serving as a control, and the following marker proteins(pI marker proteins), five lanes in total.
Marker proteins
Amyloglucosidase (3.50)
Soybean trypsin inhibitor (4.55)
β-lactoglobulin A (5.20)
Bovine carbonic anhydrase B (5.85)
Human carbonic anhydrase B (6.55)
Horse myoglobin-acidic band (6.85)
Horse myoglobin-basic band (7.35)
Lentil lectin-acidic band (8.15)
Lentil lectin-middle band (8.45)
Lentil lectin-basic band (8.65)
Trypsinogen (9.30)

Electrode solutions: Anode solution=1M $H_3PO_4$ Cathode solution=1M NaoH
Electrophoresis: With constant power of 1 W/cm gel width with cooling (10° C.) for 90 minutes.
Staining: With Silver Stain Kit
The gel resulting from the electrophoresis was sliced at a spacing of 1 cm and subjected to extraction, with 1 ml of distilled water with shaking (2 days). The isoelectric point was calculated from the pH measurement after the electrophoresis.

The isoelectric point (pI) of fraction 2 was found to be about 5.0, and the fraction migrated as a single band at this position. Fraction 1 had isoelectric points of about 5.2 and about 5.0 and migrated as two bands.

(5) Amino acid composition
Each of fractions 1 and 2 (30 μl) was carefully placed into the bottom of a thick-walled hard test tube made of Pyrex glass and 12 mm×120 mm, and was dried in a vacuum in a desiccator containing sodium hydroxide pellets. A 50 μl quantity of 4N methane-sulfonic acid (containing 0.2% 3-(2-aminoethyl)indole and produced by Pierce) was added to the dry specimen within the tube. The tubes were deaerated at 0.1 to 0.2 mm Hg for 1 minute and then sealed off. The specimen was hydrolyzed in a heater at 118° C. over a period of 24 hours. After opening the tube, the mixture was neutralized with 46 μl of 4N sodium hydroxide and diluted to an amount of 450 μl with citric acid buffer.

A 250 μl quantity of the specimen solution was used for amino acid analysis by an amino acid analyzer (Model 835, product of Hitachi Ltd.). The amino acids separated were detecteds by the o-phthalaldehyde method and quantitatively determined with reference to calibration curves prepared with use of authentic amino acids.

Table 2 shows the results in terms of the mole ratio of component amino acids based on Phe (10 moles). Under the above analysis conditions, Pro and Cys are not determinable.

TABLE 2

| Amino acid | Fraction 2 (mole ratio) |
| --- | --- |
| Asp and/or Asn | 20.6 |
| Thr | 11.4 |
| Ser | 10.1 |
| Glu and/or Gln | 16.8 |
| Gly | 6.6 |
| Ala | 14.4 |
| Val | 5.8 |
| Met | 2.3 |
| Ile | 9.3 |
| Leu | 15.0 |
| Tyr | 6.8 |
| Phe | (10) |
| Lys | 10.5 |
| His | 3.0 |
| Trp | 1.6 |
| Arg | 2.9 |

(6) Amino acid sequence
Each of fractions 1 and 2 (150 μl) was analyzed by a protein sequencer (Model 470A, Applied Biosystems Inc.). Each resulting PTH-amino acid was suitably diluted with 100 to 50 μl of 33% aqueous acetonitrile solution, and a 5-μl portion of the dilution was injected into a chromatographic column by an autosampler, Waters 710B. For the chromatographic system, two pumps, Beckman Model 112, were operated by a controller, Model 421. The column used, measuring 2 mm×250 mm and packed with Ultrasphere ODS-5 μm, was maintained at 55° C. by a column heater. The flow rate was 0.3 ml/min. A mixture of 20 mM sodium acetate and acetonitrile was used for gradient elution. Absorbance was monitored at 269 nm. Analysis was conducted for 45 minutes.

The results of 40 cycles of analysis revealed that the two fractions were identical in amino acid sequence except the 36th amino acid and that they had the following sequence.

```
                    5                          10
Ser —Ala —Pro —Phe —Ser —Phe —Leu —Ser —Asn—Val —
                    15                         20
Lys —Tyr —Asn—Phe —Met—Arg—Ile —Ile —Lys —Tyr —
                    25                         30
Glu —Phe —Ile —Leu —Asn—Asp—Ala —Leu —Asn—Gln —
                    35                         40
Ser —Ile —Ile —Arg—Ala —X —Asp—Gln —Tyr —Leu
```

The 36th amino acid (X in the above formula) of fraction 1 was Asn which had been predicted from the sequence of the gene, and that of fraction 2 was Asp.

The foregoing indicates that fraction 1 is the polypeptide of the formula (A), namely IL-1α, further revealing that the other fraction 2 is a polypeptide of the invention which corresponds to IL-1α wherein the 36th amino acid is replaced by Asp. This polypeptide of the invention will be hereinafter referred to as "polypeptide I."

The IL-1α was unstable as a substance and was found, for example, to partly change into a more stable polypeptide I when present in a trisHCl buffer (pH 8.0).

Example 2

(1) Preparation of polypeptide I of the invention

A polypetide I expression plasmid was prepared by the site-specific mutagenesis method (Pro. Nat. Acad. Sci., 81, 5662–5666 (1984); Science, 224, 1431 (1984), using plasmid ptrpIL-1α-113 obtained in Reference Example 1, and polypeptide I was prepared from the plasmid as will be described below.

M13 mp 11 phage vector was used as a single-strand DNA template. EcoRI/BamHI DNA fragment was isolated from plasmid ptrpIL-1α-113 and cloned in M13 mp 11 phage (RF) at restriction enzyme EcoRI and BamHI sites to obtain single-strand (ss) DNA (M13-IL-1α-113), which was then used as a mutagenesis template.

Synthetic oligonucleotide [5'-ACTGGGTGAGCTTGGCAG-3'(primer)] was phosphorylated with T4 polynucleotide kinase and hybridized with ss M13-IL-1α-113 DNA. The hybrid was annealed, thereafter treated with DNA polymerase I, (Klenow fragment) and T4 DNA ligase in the presence of dNTPs and incubated at 15° C. for 18 hours.

The DNA obtained was introduced into JM105 competent cell for transformation. The resulting phage plaque (50 colonies) was inoculated onto the intro-cellulose filter on the agar plate and incubated at 37° C. for 18 hours. A filter containing the cloning was treated with an alkali in the usual manner for denaturation, dried and then baked at 80° C. for 2 hours. The filter was prehybridized and then hybridized at room temperature with $^{32}P$ probe prepared by labeling the primer with $^{32}P$-γ-ATP. The filter hybridized was washed with 6×SSC buffer at room temperature for 10 minutes and further at 54° C. for 5 minutes, dried and thereafter subjected to autoradiography at −70° C. for 18 hours.

M13-IL-1α-36D was selected as a typical clone from among five mutant clones, infected with JM105 and incubated to prepare ssDNA and RF DNA.

M13 dideoxynucleotide sequencing was performed for ssDNA to confirm mutation of the contemplated gene.

EcoRI/BamHI fragment was prepared from RF DNA produced in JM105 and introduced into expression plasmid in the same manner as in the foregoing reference example to obtain the desired polypeptide I expression plasmid (IL-1α-36D).

Using this plasmid, polypeptide I was expressed in the same manner as in Example 1, followed by purification (DEAE-HPLC gave a single GIF activity peak), whereby the desired polypeptide I was obtained with the foregoing characteristics. The product was found to have specific activity of about $1 \times 10^7$ GIF units/mg protein.

Example 3

(1) Preparation of polypeptides II and III of the invention

Plasmid ptrpIL-1α-141S for expressing a polypeptide of the invention, corresponding to IL-1α wherein the 141st amino acid (Cys) is replaced by Ser, was prepared in the same manner as in Example 2 using 5'-ACTGGGTGAGCTTGGCAG-3' as the primer.

The same expression and purification procedures as in Example 1 were repeated using this plasmid, DEAE-HPLC similarly conducted gave two GIF activity peaks. The peak fractions were analyzed in the same manner as above, with the result that the peak fraction which was earlier in retention time was identified as a polypeptide of the invention (polypeptide III) anticipated from the gene sequence, i.e. one corresponding to IL-1α wherein the 141st amino acid (Cys) was replaced by Ser.

The analysis revealed that the other peak fraction was a polypeptide of the invention corresponding to IL-1α wherein the 36th amino acid (Asn) and the 141st amino acid (Cys) were replaced by Asp and Ser, respectively. This polypeptide will hereinafter be referred to as "polypeptide II."

Example 4

(1) Preparation of polypeptide II of the invention

Plasmid ptrpIL-1α-36D.141S for expressing the desired polypeptide II was prepared in the same manner as in Example 3, using plasmid ptrpIL-1α-141S obtained in Example 3 and using 5'-ATTCGAGCCGATGATCAG-3' as the primer.

HB101 strain was caused to harbor the above plasmid, ptrpIL-1α-36D.141S. The strain has been deposited under the name of "*Escherichia coli* HB101/IL-1α-36D141S" with deposition number FERM BP-1295 in Fermentation Research Institute, Agency of Industrial Science & Technology.

The same expression and purification procedures as in Example 1 were repeated with use of the above plasmid to obtain the desired polypeptide II of the invention.

SDS-PAGE indicated that the polypeptide was about 18 kd in molecular weight. The isoelectric point (PI) thereof was found to be about 5.0 by IEF.

Polypeptides II and III were equivalent to polypeptide I in specific activity (GIF activity).

Pharmaceutical test example 1

(1) GIF-activity and LAF activity

The GIF activity of the present polypeptide has already been described. The LAF activity of the polypeptides I, II and III was comparable to the GIF activity thereof.

The polypeptide of the invention was tested as follows.

(2) Test for antitumor activity

Tumor cells (200,000), "Meth A", were intra-cutaneously transplanted into each of BALB/c mice (zero day). On the 7th day and 8th day after transplantation, the polypeptide I was given to the tumor site of the mice in the first experiment in an amount of 0.3, 1 or 3 μg per mouse.

Seven mice in each group were used. A solvent (1% mouse serum) was administered in the same manner to the control group.

Figure 3:
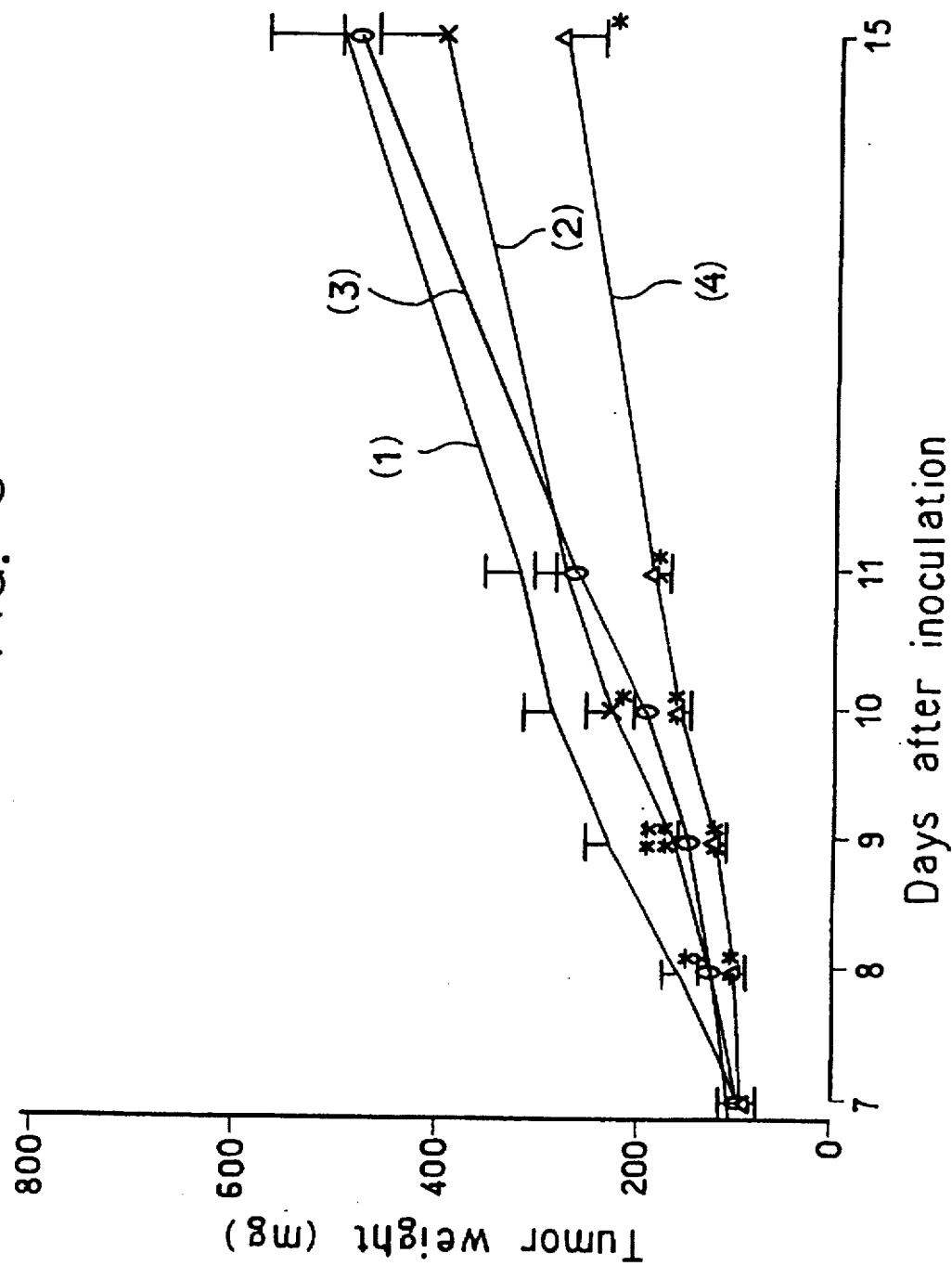
FIG. 3 shows the results of an antitumor activity test.

The test results are shown in FIG. 3, in which the number of days clasped after the inoculation of tumor cells is plotted as abscissa vs. the weight of the tumor (mg) as ordinate. A control group is represented by curve (1), a group with a dose of 0.3 µg of polypeptide I by curve (2), a group with a dose of 1 µg of polypeptide I by curve (3), and a group with a dose of 3 µg of polypeptide I by curve (4). The weight of tumor is expressed in terms of mean±standard deviation (SD). The mark * represents P<0.05 in Students' T-test, and the mark ** P<0.01.

(3) Test for effect to promote CSF production (3)-1

The following test was conducted using cell strain U-373MG (ATCC HTB17, glioblastoma, astrocytoma, human).

Cells of the above strain were suspended in Eagle's MEM medium (product of Nissui Pharm. Co.) containing 10% FCS (product of GIBCO), MEM non-essential amino acids (product of Flow) and MEM sodium pyruvate (product of Flow), to a concentration of $2 \times 10^5$ cells/ml. The polypeptide I to be tested was added in varying concentrations to portions of the suspension. Each of the mixtures was incubated in a carbon dioxide incubator at 37° C. for 24 hours.

The culture supernatant was collected, and the amount of CSF produced and accumulated in the supernatant was measured using mouse bone marrow cells (Lewis, I. C. et al., J. Immunol, 128, 168 (1982).

Figure 4:
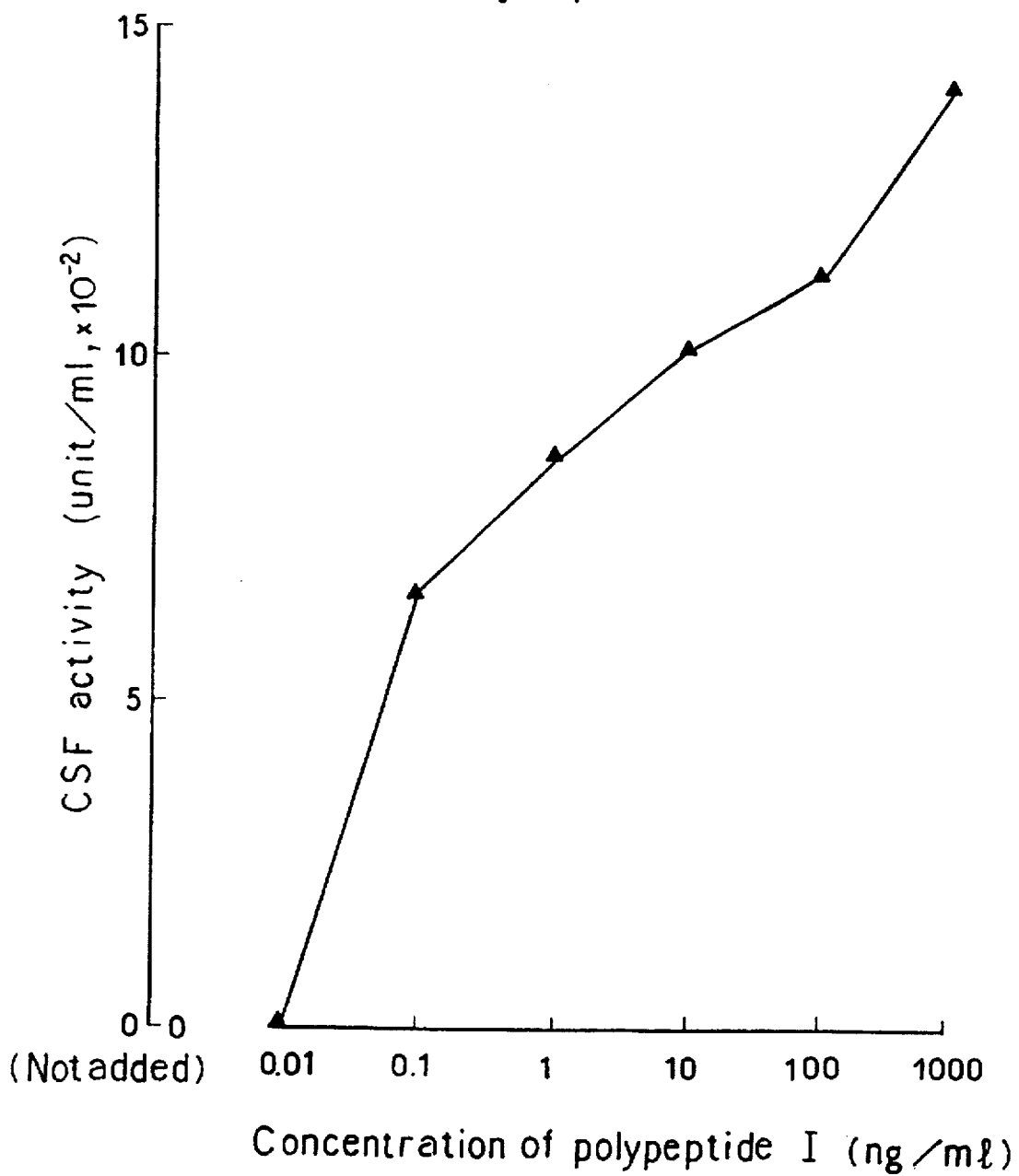
FIGS. 4 and 5 show the results obtained by testing the polypeptide of the invention for effect to promote production of CSF.

The results are given in FIG. 4, in which the concentration (ng/ml) of polypeptide I is plotted as abscissa vs. the CSF activity $(U/ml, \times 10^{-2})$ as ordinate.

(3)-2

The following animal experiment was conducted to substantiate that polypeptide I, when administered to the living body, acts to promote production of CSF in vivo.

To normal mice (BALB/C strain, purchased from Experimental Animal Cooperative Association of Shizuoka Prefecture, Japan) was intravenously given polypeptide I in varying amounts. Blood was collected from the animal 8 hours after the administration and checked for the CSF activity as in (3)-1 above. As a control, human serum albumin (HSA) was administered in the same manner to a control group for the test.

Figure 5:
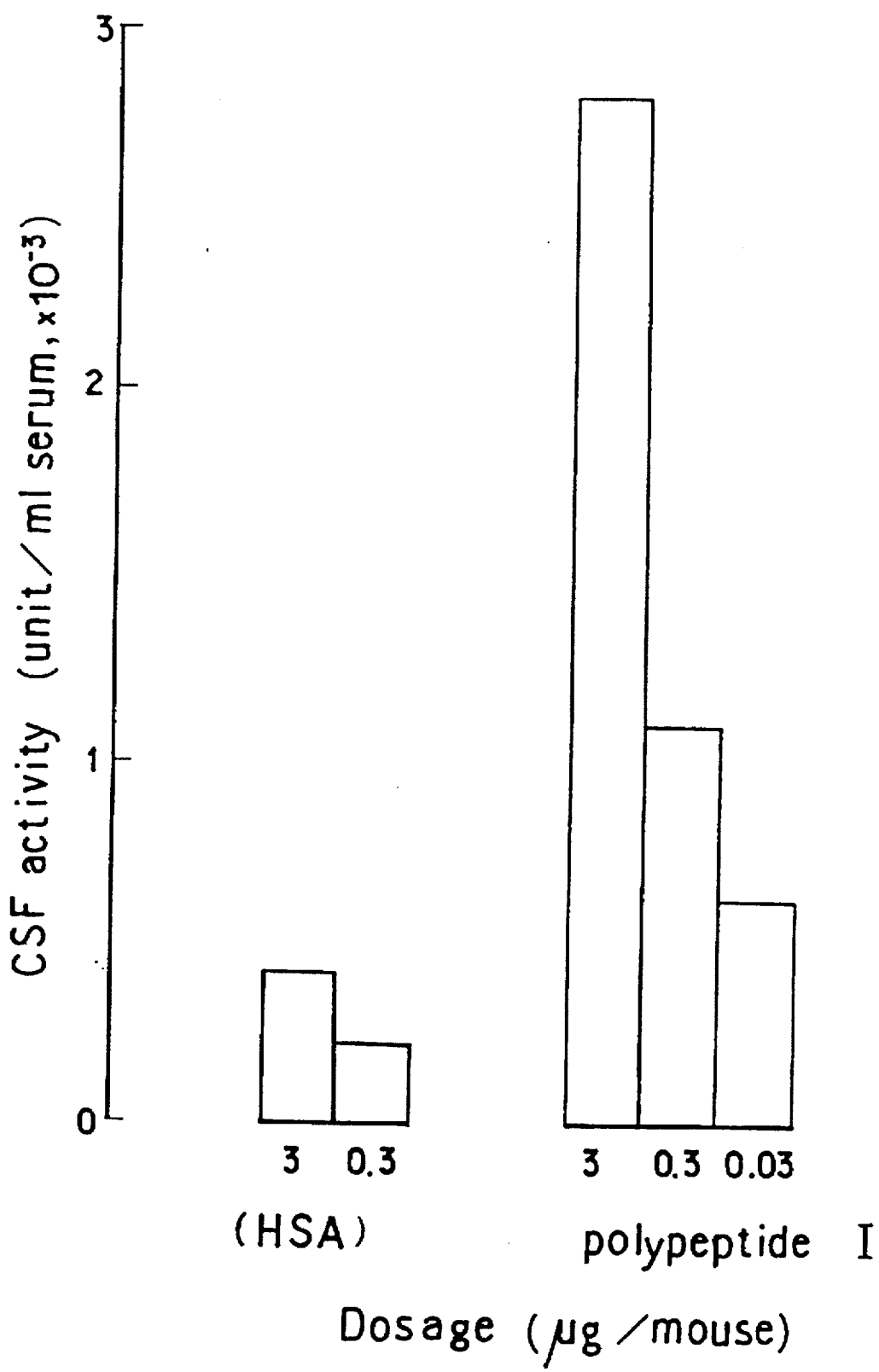

The results are shown in FIG. 5 in which the amount of the polypeptide I or the amount of HSA administered (µg/mouse) is plotted as abscissa and CSF activity (unit/ml serum, $\times 10^{-3}$) as ordinate.

(4) Test for anti-inflammatory effect

The following test was conducted according to the method of Winter et al. (Proc. Soc. Exptl. Biol. Med., 111, 544–547 (1962).

Six- to eight-week-old male rats (Spraque Dawley strain, Nippon Charles River Co., Ltd.) were used as divided into groups of 6 to 8 rats each according to the body weight one day before the experiment. A suspension of 1% Carrageenan (product of Marine Colloid) in saline, serving as an agent for causing inflammation, was subcutaneously injected in an amount of 0.1 ml into the sole of the right rear leg of the rat to cause swelling of the foot. To evaluate the swelling, the volume of the sole was measured a predetermined period before and after the injection using a plethysmometer (product of Ugo-Vasile). The ratio of the increased volume due to the injection relative to the value before the injection was calculated as swelling %.

The substance to be tested was dissolved in Dulbeco's phosphate buffered saline, and 0.1 ml of the solution was subcutaneously injected into the back of the rat 1 hour before the injection of the inflammation causing agent. The solvent was given to a control group.

Figure 6:
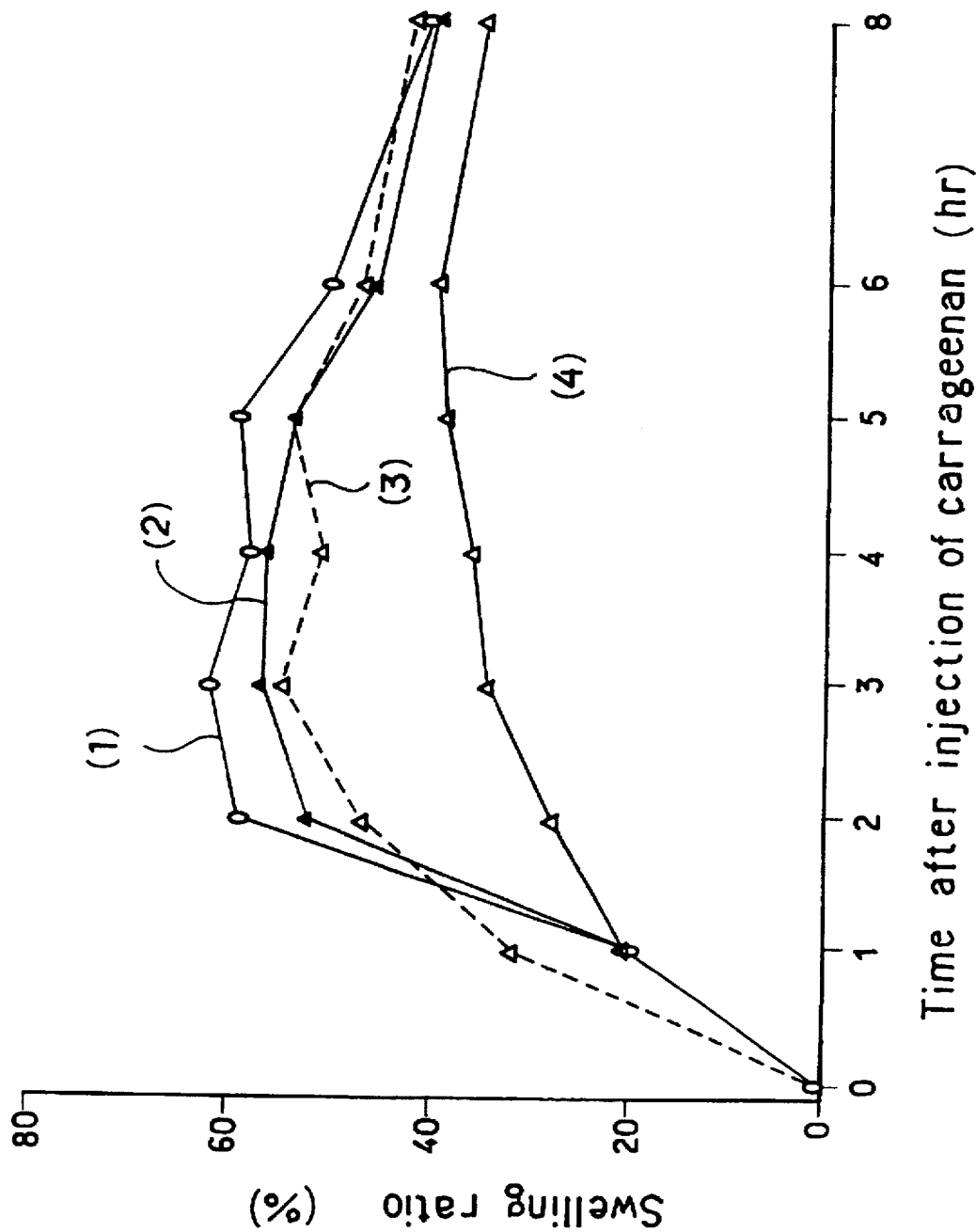
FIG. 6 shows the results obtained by testing the polypeptide of the invention for anti-inflammatory effect.

The results are shown in FIG. 6, in which the time (hours) elapsed after the injection of the inflammation causing agent is plotted as abscissa vs. the swelling % as ordinate. In the diagram, the control group is represented by curve (1), a group to which 0.1 µg of polypeptide I was given by curve (2), a group with 1 µg of polypeptide I by curve (3), and a group with 10 µg of polypeptide I by curve (4).

(5) Test for effect to prevent radiation injury

One µg or 0.3 µg of polypeptide I was intra-peritoneally given to each of 9-week-old mice of BALB/c strain 20 hours before the mice were exposed to a lethal dosage of X-rays.

The mice were systemically exposed to X-rays at a dose of 850 roentgens by an X-ray irradiator (MBR-1505R, product of Hitachi Medico Co., Ltd.) and thereafter checked for survival daily. PBS was given to a control group.

The results are shown in FIG. 7, in which the number of days after the irradiation is plotted as abscissa vs. the survival ratio (%) as ordinate. The group to which 1 µg of polypeptide I was given is represented by curve (1), the group with 0.3 µg of polypeptide I by curve (2), and the control group by curve (3).

FIG. 7 shows that all the mice of the control group died on the 18th day after the X-ray irradiation, whereas polypeptide I was found effective for preventing radiation injury depending on the dosage. It was found that about 80% of the group with the dose of 1 µg were saved from death due to radiation injury and survived.

(6) Test for effect to prevent opportunistic infection

The following test was conducted using model mouse.

On the first day, 100 mg/kg of 5-fluorouracil (5-Fu, product of Kyowa Hakko Co., Ltd.) was intravenously given to 6-week-old male mice of ICR strain (7 mice in each group). On the 2nd, 4th and 6th days, polypeptide I of the invention was subcuteneously administered to the mice at a dose of 1 µg/mouse. On the 7th day, a specified quantity of *Pseudomonas aeruginosa* E-2 was intra-peritoneally given to the mice for infection. On the 10th day, the number of animals survived was counted to determine the survival ratio (%).

The results are given in FIGS. 8(a) to (c). FIG. 8(a) shows the result achieved by the group thus treated. FIG. 8(b) shows the result achieved by a control group to which polypeptide I was not given (but 5-Fu only was given). FIG. 8(c) shows the result achieved by another control group to which neither 5-Fu nor polypeptide I was given.

In FIGS. 8(a) to (c) the survival ratio (%) is plotted as ordinate vs. groups A to F which were each given the following amount of the pseudomonas as abscisso.

| Group | Number of cells/mouse |
| --- | --- |
| A | 19,000 |
| B | 3,800 |
| C | 750 |
| D | 150 |
| E | 30 |
| F | 6 |

(7) Testing IL-1α for effect to promote CSF production

The following test was conducted using human embryonic lung fibroblasts (HFL-1, ATCC registered cell strain No.CCL-153) which produce CSF.

HFL-1 cells were suspended in hamster 12K culture (Ham, R. G., Proc. Natl. Acad. Sci., 53, 288 (1965) containing 10% FCS to a concentration of $2 \times 10^5$ cells/ml.

IL-1α obtained in Example 1 was added to portions of the cell suspension in varying concentrations. Each of the mixtures was incubated in a carbon dioxide gas incubator at 37° C. for 24, 48 or 72 hours. The culture supernatant was collected, and the amount of CSF produced and accumulated in the supernatant was measured using mouse bone marrow cells (Lewis, I. C. et al, J. Immunol., 128, 168 (1982).

The results are listed in Table 3 below.

TABLE 3

| Time (day) | Concentration of incubated IL-1α (GIF units/ml) | | |
|---|---|---|---|
| | 0 | 1 | 10 |
| | CSF activity (U/ml) | | |
| 1 | 0 | 190 | 130 |
| 2 | 0 | 240 | 145 |
| 3 | 0 | 100 | 120 |

The above results reveal that the addition of IL-1α promotes CSF production by HFL-1 cell strain. (8) Method of preparing cytokines from animal cells HSB-2 C5B2 cells (J. Immunol., 131, 1682–1689 (1985), in an amount of $2\times10^5$ cells/well, were incubated for 24 hours in the presence of varying concentrations of polypeptide II and 0.01% PHA-P. The IL-2 activity of the supernatant collected was measured by the method of K. A. Smith et al. using IL-2 dependent mouse T cells (CTLL 2) (J. Immunol., 120, 2027 (1978). Table 4 below shows the results.

TABLE 4

| Concentration of polypeptide II (ng/ml) | IL-2 activity (cpm × $10^{-3}$) mean (n = 5) |
|---|---|
| 0 | 0.4 |
| 0.0005 | 0.4 |
| 0.005 | 0.6 |
| 0.05 | 2.1 |
| 0.5 | 3.2 |
| 5 | 3.5 |
| 50 | 3.9 |
| 500 | 3.8 |

These results indicate that the use of the polypeptide of the invention permits animal cells to produce natural-type cytokines efficiently. The amount of the present polypeptide to be used for the above method can be very small, usually about 10 ng/ml, whereby satisfactory results are achievable, while the use of the polypeptide facilitates purification of the cytokine derived.

(9) When cytokines are to be produced from animal cells, it is essential that the polylpeptide of the invention used for inducing the production be stable in structure under the prevailing condition and be bound to the IL-1 receptor on the surface of the cells. More specifically, it is required that the present polypeptide bind to the IL-1 receptor and transmit to the cell a signal necesary for the production of the cytokine. Accordingly, the following test was conducted in connection with the binding of the present polypeptide to the IL-1 receptor on fibroblasts.

Balb/3T3 cells (clone A31: ATCC, CCL-163, $1\times 10^6$ cells/well) almost uniformly grown over a 6-well plate were reacted at 4° C. for 2 hours with 50000 cpm/well of $^{125}$I-labelled IL-1β (Seikagaku (Biochemistry) 58, No.8, p. 840 (1986); EPO No.187991) and 20 ng/ml of IL-1β or polypeptide II preincubated at 37° C. for 24 hours in D-MEM supplemented with 10% FCS. The liquid reaction mixture was discarded with a Pasteur pipette, the cells were gently washed with 1 ml of D-MEM supplemented with 10% FCS, and the supernatant was discarded. After repeating the washing procedure twice, the cells were solubilized with 1 ml of a mixture of 1% SDS and 0.2 N NaOH. The radioactivity (bound radioactivity) of the solubilized cell solution and the liquid used for washing the wells was measured by a gamma-counter.

The $^{125}$I-labeled IL-1β used was prepared and purified by the method of Bolton and Hunter (Biochem. J., 133, 529 (1973). Specific activity: at least 250 μCi/μg protein.

TABLE 5

| | Inhibition activity (%) |
|---|---|
| Polypeptide II | 100 |
| IL-1β | About 4 |

$$\text{Inhibition activity (\%)} = \frac{A - B}{A - C} \times 100$$

wherein

A: Bound radioactivity in absence of unlabelled polypeptide I

B: Experimental value of bound radiocativity

C: Radioactivity unspecifically absorbed on the plate

This index represents the binding activity of the conjointly present IL-1β or polypeptide II on the IL-1 receptor. Incidentally, it is known that IL-α and IL-1β are in common in respect of the IL-1 receptor.

Table 5 reveals that polypeptide II retains the satisfactory binding activity on IL-1 receptor even under cytokine induction-production conditions and is therefore useful for such application.

Preparation Example 1

To a solution of $1\times10^7$ units/ml, calculated as GIF activity, of polypeptide I in saline was added human serum albumin (HSA) to a concentration of 0.5%. The mixture was filtered (0.22 μm membrane filter), placed into vials, 1 ml, in each, in sterile state, and lyophilized to obtain a preparation for injection. The preparation is used as dissolved in 1 ml of distilled water for injection.

We claim:

1. A method for promoting production of colony stimulating factor comprising administering, to a subject in need of promotion of production of colony stimulating factor, a pharmaceutically effective amount of purified IL-1α having an amino acid sequence represented by formula (A):

formula (A)

```
                    5                       10
Ser—Ala—Pro—Phe—Ser—Phe—Leu—Ser—Asn—Val—
                   15                      20
Lys—Tyr—Asn—Phe—Met—Arg—Ile—Ile—Lys—Tyr—
                   25                      30
Glu—Phe—Ile—Leu—Asn—Asp—Ala—Leu—Asn—Gln—
                   35                      40
Ser—Ile—Ile—Arg—Ala—Asn—Asp—Gln—Try—Leu—
                   45                      50
Thr—Ala—Ala—Ala—Leu—His—Asn—Leu—Asp—Glu—
```

-continued

```
                    55                          60
        Ala—Val—Lys—Phe—Asp—Met—Gly—Ala—Tyr—Lys—

65                          70
        Ser—Ser—Lys—Asp—Asp—Ala—Lys—Ile—Thr—Val—

75                          80
        Ile—Leu—Arg—Ile—Ser—Lys—Thr—Gln—Leu—Tyr—

85                          90
        Val—Thr—Ala—Gln—Asp—Glu—Asp—Gln—Pro—Val—

95                         100
        Leu—Leu—Lys—Glu—Met—Pro—Glu—Ile—Pro—Lys—

105                         110
        Thr—Ile—Thr—Gly—Ser—Glu—Thr—Asn—Leu—Leu—

115                         120
        Phe—Phe—Trp—Glu—Thr—His—Gly—Thr—Lys—Asn—
```

-continued

```
                   125                         130
        Tyr—Phe—Thr—Ser—Val—Ala—His—Pro—Asn—Leu—

135                         140
        Phe—Ile—Ala—Thr—Lys—Gln—Asp—Tyr—Trp—Val—

145                         150
        Cys—Leu—Ala—Gly—Gly—Pro—Pro—Ser—Ile—Thr—

155
        Asp—Phe—Gln—Ile—Leu—Glu—Asn—Gln—Ala.
```

\* \* \* \* \*